United States Patent
Parra et al.

(10) Patent No.: US 10,835,147 B1
(45) Date of Patent: Nov. 17, 2020

(54) METHOD FOR PREDICTING EFFICACY OF A STIMULUS BY MEASURING PHYSIOLOGICAL RESPONSE TO STIMULI

(71) Applicant: NEUROMATTERS, LLC, New York, NY (US)

(72) Inventors: Lucas Parra, New York, NY (US); Paul Sajda, New York, NY (US); Paul DeGuzman, Valley Cottage, NY (US); Daniel Rosenthal, New York, NY (US); Charles Phillip Cloud, New York, NY (US); Jacek Dmochowski, Montclair, NJ (US)

(73) Assignee: NEUROMATTERS, LLC, New York, NY (US)

( * ) Notice: Subject to any disclaimer, the term of this patent is extended or adjusted under 35 U.S.C. 154(b) by 207 days.

(21) Appl. No.: 14/836,316

(22) Filed: Aug. 26, 2015

Related U.S. Application Data

(60) Provisional application No. 62/041,706, filed on Aug. 26, 2014.

(51) Int. Cl.
*A61B 5/0484* (2006.01)
*A61B 5/0402* (2006.01)
(Continued)

(52) U.S. Cl.
CPC ............ *A61B 5/04842* (2013.01); *A61B 3/11* (2013.01); *A61B 3/113* (2013.01); *A61B 5/0205* (2013.01); *A61B 5/0402* (2013.01); *A61B 5/04845* (2013.01); *A61B 5/7225* (2013.01); *A61B 5/7275* (2013.01); *A61B 2503/12* (2013.01)

(58) Field of Classification Search
CPC ....... A61B 5/04842; A61B 3/11; A61B 3/113; A61B 5/0205; A61B 5/0402; A61B 5/04845; A61B 5/7225; A61B 5/7275; A61B 2503/12

USPC .............. 600/300–301; 702/127, 189–194; 340/539.11–539.13, 573.1
See application file for complete search history.

(56) References Cited

U.S. PATENT DOCUMENTS

| 8,959,540 B1* | 2/2015 | Gargi | H04N 21/251 |
| | | | 725/19 |
| 2010/0211439 A1* | 8/2010 | Marci | G06Q 10/10 |
| | | | 705/7.29 |
| 2016/0021425 A1* | 1/2016 | Eriksson | H04H 60/46 |
| | | | 725/10 |

OTHER PUBLICATIONS

Aljadeff et al. (2013), Spike Triggered Covariance in Strongly Correlated Gaussian Stimuli, PLoS Comput Biol 9(9):e1003206.*

* cited by examiner

*Primary Examiner* — Michael W Kahelin
*Assistant Examiner* — Vynn V Huh
(74) *Attorney, Agent, or Firm* — Brown Rudnick LLP

(57) ABSTRACT

Methods are disclosed for determining an efficacy of a stimulus based on one or more measurable physiological responses to one or more stimuli including one or more stimulus features. Data is acquired on physiological responses of a group of one or more subjects to presentation of one or more stimuli including one or more stimulus features. The data on the one or more physiological responses of the one or more subjects is correlated with the presentation of the one or more stimulus features included in the one or more stimuli. The correlated data on the one or more physiological responses are associated with a separately-determined efficacy of the one or more stimuli to form a stimulus efficacy model. From this information, a projected efficacy of a stimulus is determinable by comparing one or more subsequently-measured physiological responses to the stimulus with the stimulus efficacy model.

11 Claims, 9 Drawing Sheets

(51) Int. Cl.
*A61B 5/00* (2006.01)
*A61B 5/0205* (2006.01)
*A61B 3/113* (2006.01)
*A61B 3/11* (2006.01)

METHOD FOR PREDICTING EFFICACY OF A STIMULUS BY MEASURING PHYSIOLOGICAL RESPONSE TO STIMULI

RELATED APPLICATION

This application claims the benefit of U.S. Provisional Patent Application Ser. No. 62/041,706, titled "METHOD FOR MEASURING PHYSIOLOGICAL IMPACT OF STIMULUS FEATURES TO PREDICT RESPONSE OF SUBJECTS TO STIMULI INCLUDING SUCH STIMULUS FEATURES," filed on Aug. 26, 2014, the entire contents of which are hereby incorporated in its entirety herein.

GOVERNMENT RIGHTS

This invention was made with government support under contract number W31P4Q-13-C-0038, awarded by the Defense Advanced Research Projects Agency (DARPA). The government has certain rights in the invention.

BACKGROUND

Every day, countless sums of money are expended in trying to influence opinions or behavior of individuals or groups, or to determine what types of images, sounds, or other stimuli may successfully influence the opinions or behavior of individuals or groups. Just to list a few examples, movie producers, advertisers, politicians, video game developers, and many others invest huge amounts of time and money in trying to engage their audience and generate a positive response to their offerings. To this end, for instance, a great deal of time, money, and energy is invested in conducting focus groups, administering consumer surveys, evaluating user behavior, and in conducting other processes in the attempt to create media events that will attract consumers or other supporters.

Despite the desire to be able to predict a response to media stimuli or other stimuli, it has proven difficult to make predictions of what stimuli will engage an audience and elicit a desirable response. Existing methods often prove unsatisfactory. For example, in focus groups, participants may be asked to rate or rank advertisements based on their individual preferences and the quality of the ads. However, asking participants to rate or rank advertisements may not yield accurate responses for several reasons. First, when participants are brought into a focus group or otherwise asked to watch the advertisements, they are actively requested to watch the advertisements and, thus, may react differently than ordinary viewers, who may passively watch the advertisement when it is inserted in a break within a program. The different mindset can result in the focus group having a very different response to the advertisement than an ordinary viewer. Similarly, being asked to deliberately form an opinion or a preference may bias a subject to report what the subject believes that the person administering wants to hear.

It thus would be a significant advance in the art to be able to derive a more accurate way of gauging a response of one or more subjects to a set of stimuli as may be included in an audio and/or video an advertisement, a television program, video game, a movie, music, or other media, or in any other form of stimuli.

SUMMARY

Methods are disclosed for determining an efficacy of a stimulus based on one or more measurable physiological responses to one or more stimuli including one or more stimulus features. Data is acquired on physiological responses of a group of one or more subjects to presentation of one or more stimuli including one or more stimulus features. The data on the one or more physiological responses of the one or more subjects is correlated with the presentation of the one or more stimulus features included in the one or more stimuli. The correlated data on the one or more physiological responses are associated with a separately-determined efficacy of the one or more stimuli to form a stimulus efficacy model. From this information, a projected efficacy of a stimulus is determinable by comparing one or more subsequently-measured physiological responses to the stimulus with the stimulus efficacy model.

In another aspect, a method to project an efficacy of a stimulus based on one or more measurable physiological responses is disclosed. Data is acquired on physiological responses of a group of one or more subjects to presentation of one or more stimuli included one or more stimulus features. A first data matrix is formed, where the first data matrix includes one or more stimuli tracked against a time over which the one or more stimulus features included in the one or more stimuli were presented. A second data matrix including one or more physiological responses of the one or more subjects to which the one or more stimulus features included in the one or more stimuli were presented tracked against the time over which the one or more stimulus features included in the one or more stimuli were presented. A separately-determined efficacy of the one or more stimuli as determined from at least one of the one or more subjects and an additional group of one or more subjects is associated with the one or more resulting physiological responses. Statistical processing is applied to generate a model associating the separately-determined efficacy of the one or more stimuli with the one or more physiological responses to determine a projected efficacy of a stimulus based on subsequently-measured physiological responses to the stimulus.

In still another aspect, a method of predicting a response of one or more subjects to a stimulus includes subjecting a group of one or more subjects to one or more stimuli including one or more stimulus features. Data is acquired on one or more physiological responses of the group of one of more subjects to presentation of the one or more stimulus features included in the one or more stimuli. An efficacy of the stimuli is determined from at least one of the one or more subjects and an additional group of one or more subjects. A model is generated correlating the one or more physiological responses to the presentation of the one or more stimulus features included in the one or more stimuli. The model is associated with the efficacy of the one or more stimuli to form a stimulus efficacy model. The stimulus efficacy model may be used to predict efficacy of a stimulus by measuring one or more physiological responses of prospective subjects to the stimulus and comparing the one or more physiological responses of the prospective subjects with the stimulus efficacy model.

Other methods are further described in detail below.

DETAILED DESCRIPTION

Methods of the present disclosure assist in predicting the response of one or more subjects to one or more visual or audible stimuli including one or more stimulus features to be presented to the one or more subjects.

Figure 1:
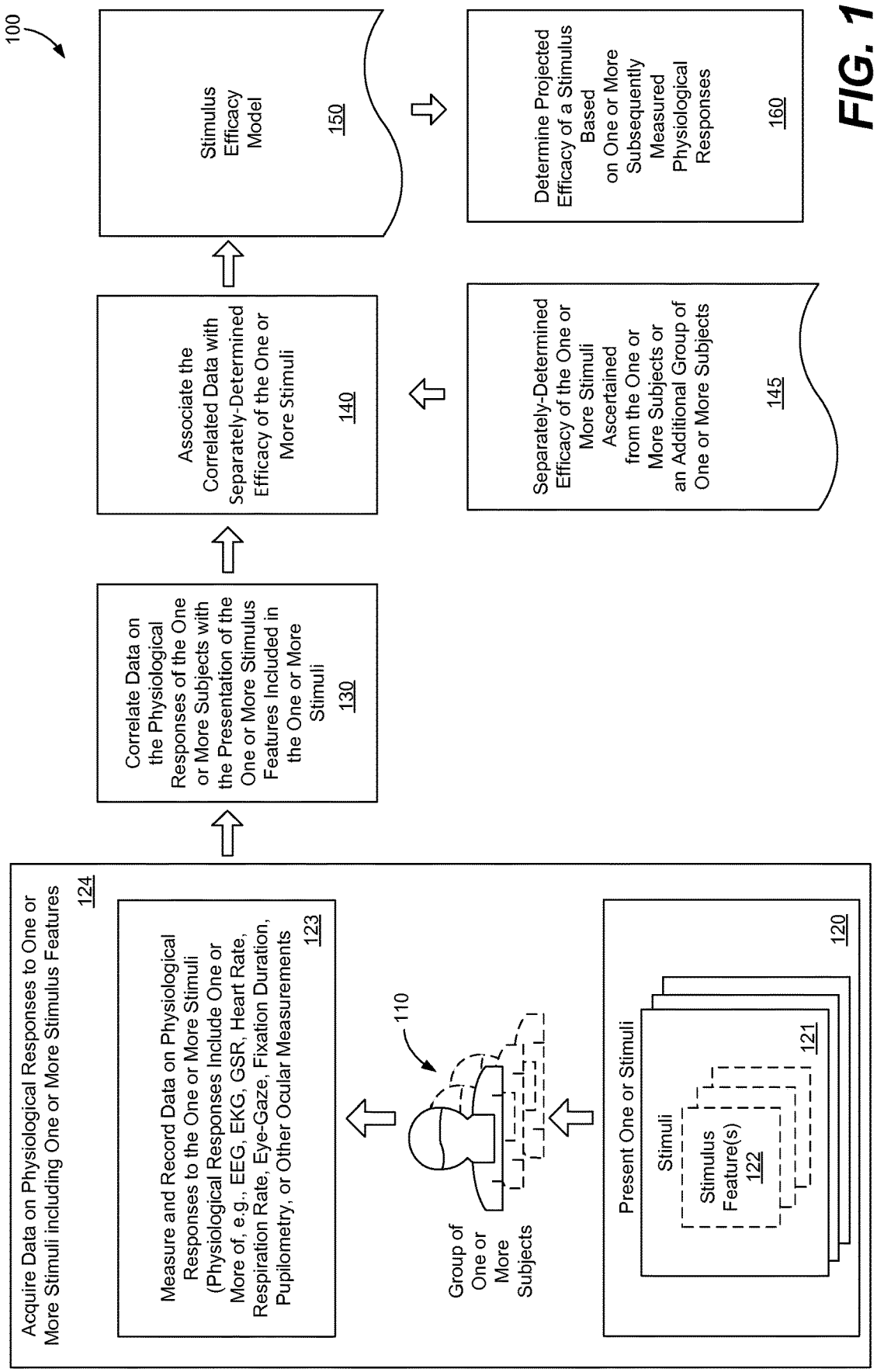
FIGS. 1 and 2 are schematic diagrams depicting analysis of responses of a group of one or more subjects to one or more stimuli including one or more stimulus features according to aspects of the disclosure.

FIG. 1 is a schematic diagram of a process 100 depicting an analysis of physiological responses of a group of one or more subjects 110 to presentation 120 of one or stimuli 121. In the process to acquire data on physiological responses to one or more stimuli 124, the group of one or more subjects 110 is subjected to one or more stimuli 121, such as visual or auditory stimuli. The one or more stimuli 121 possess one or more stimulus features 122. For example, an auditory stimulus, such as a particular sound, may include stimulus features such as pitch trajectory, sound envelope, speech envelope, spectral power, rhythm, volume, and pitch. It is known that a human mind and body have measureable reactions to stimuli, including changes in heart rate, respiration rate, eye activity, brain activity, and other biophysical reactions. A process to measure and record data on the physiological responses 123 may include electroencephalography (EEG), electrocardiography (EKG), galvanic skin response (GSR), and other techniques to measure heart rate, respiration rate, eye activity, or other physiological responses to stimuli.

A process 130 correlates the data acquired on the physiological responses with the presentation of the one or more stimulus features included in the one or more stimuli, such as by correlating a time at which the one or more stimulus features 122 of the one or more stimuli 121 were presented with the acquired physiological responses. Using statistical processes described further below with reference to FIGS. 3 and 4, a process 140 is used to associate the correlation between the resulting one or more physiological responses and the one or more stimuli 121 including the one or more stimulus features 122 to a separately-determined efficacy of the one or more stimuli 145. The separately-determined efficacy of the one or more stimuli 145 is ascertained from the group of one or more subjects 110 and/or a separate group of one or more subjects. The separately-determined efficacy data is determined by polling subjects, interviewing subjects, subjecting subjects to testing to determine their responses while being subjected to one or more stimuli, as further described with reference to FIG. 5.

The determined association of the degree of correlation between the physiological responses and the one or more stimuli 121 including the one or more stimulus features 122 with the separately-determined efficacy of the one or more stimuli 121 may be used to create a stimulus efficacy model 150. The stimulus efficacy model 150 thus may be used in a process to determine a projected efficacy of a stimulus 160. In such a process 160, subsequently-acquired physiological data acquired in response to a stimulus may be used to determine the efficacy of that stimulus to determine whether the stimulus is desirable for inclusion in an audio, visual, or audiovisual presentation, such as an advertisement, a program, a video game, etc. Thus, using the stimulus efficacy model 150 generated via the process 100 may enable one to create a media presentation that includes a stimulus or stimuli that have a desired efficacy.

Figure 2:
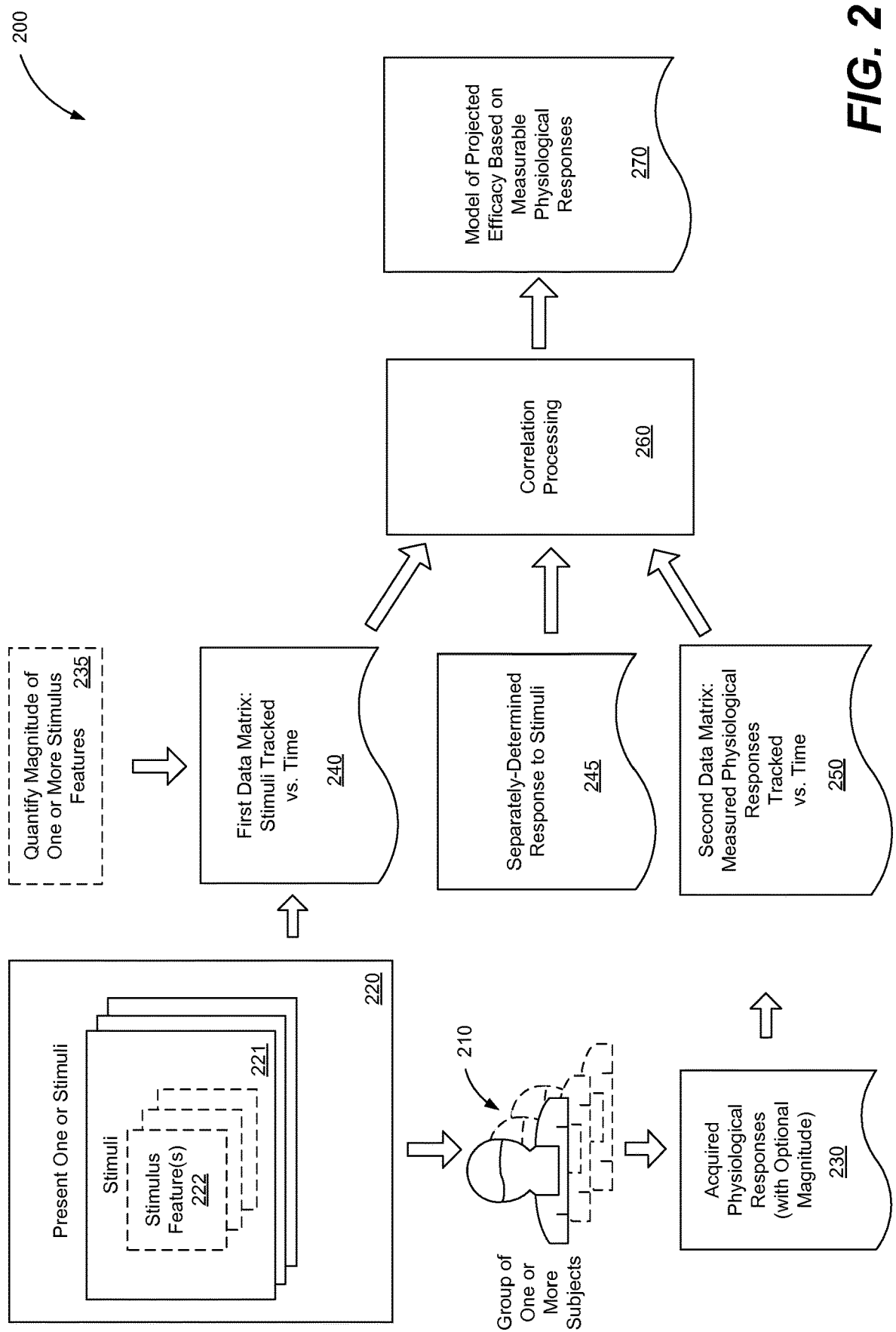

FIG. 2 is a schematic diagram of a process 200 depicting an analysis of responses of a group one or more subjects 210 to presentation 220 of one or more stimuli 221 including one or more stimulus features 222 according to another aspect of the disclosure. In the process 200, while the group of one or more subjects 210 is presented 220 with the one or more stimuli 221 including the one or more stimulus features 222, physiological responses 230 of the group of one or more subjects 210 are acquired as described with reference to FIG. 1. The magnitude of the physiological responses may be included in the acquired physiological data 230. In addition, a separately-determined efficacy 245 of each of the one or more stimuli 221 is determined. As previously stated, a process by which a separately-determined efficacy of the one or more stimuli 221 is described with reference to FIG. 5.

In order to develop a model that may identify physiological responses to the one or more stimulus features 222 included in the one or more stimuli 221, a first data matrix 240 tracking the presentation of the one or more stimuli 221 including the one or more stimulus features 222 is created, tracking the one or more stimuli 221 and the one or more stimulus features 222 over a period of time during which they are presented. Also, a second data matrix 250 tracking the physiological responses of the group of one or more subjects 210 is formed, tracking the measured responses over the time period during which the one or more stimulus features 222 included in the one or more stimuli 221 are presented. The collected data in the first matrix 240 may include a quantified magnitude 235 of each of the one or more stimulus features 222 included in the one or more stimuli 220, and the second matrix 250 may incorporate the quantified degree of the physiological responses to the one or more stimulus features 222 included in the one or more stimuli 221 in the acquired physiological data 230.

The first data matrix 240 and the second data matrix 250 are subject to correlation processing 260, which may include statistical regression of the physiological responses to the one or more stimulus features 222 included in the one or more stimuli 221. The correlation processing results in a model 270 that includes the physiological responses correlated with the stimuli.

As described with reference to FIG. 1, the model can be used to evaluate whether any of the stimuli 121 is likely to achieve a desired effect by measuring the physiological responses of subjects to the one or more stimuli 121. The resulting model may be consulted to determine what type or stimuli should be included in an audio, visual, or audiovisual work being developed so that the work will have a desired effect on its audience.

Figure 3:
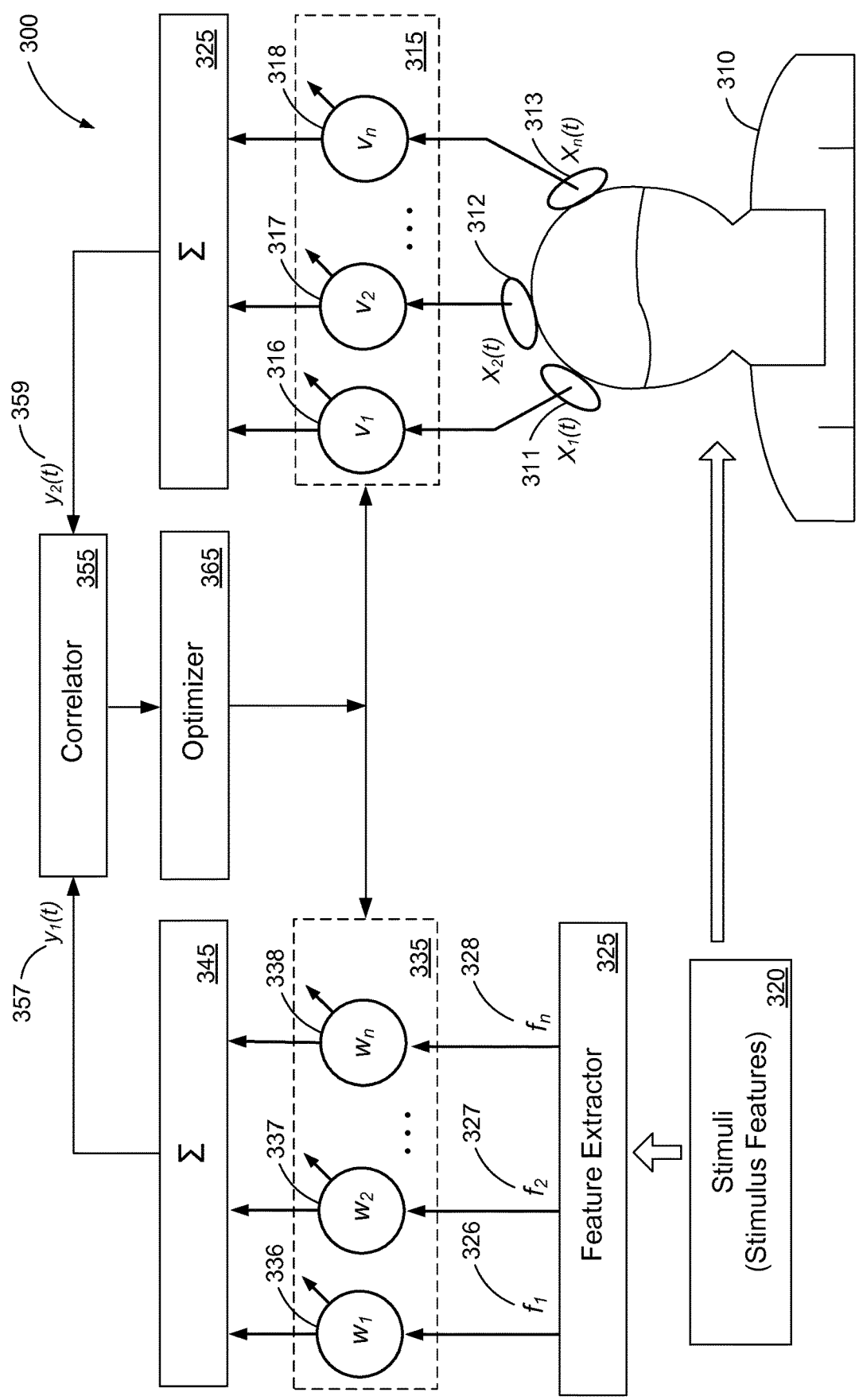
FIGS. 3 and 4 are block diagrams of systems used to analyze responses of one or more subjects to one or more stimulus features included in one or more stimuli according to aspects of the disclosure.

FIG. 3 is a block diagram of a system 300 used to analyze responses of one or more subjects to sets of stimuli including one or more stimulus features according to an aspect of the disclosure. One or more subjects, such as subject 310, are subjected to a stimulus 320, which may incorporate one or more identifiable stimulus features. The stimulus 320 may, for example, include an audio, visual, or audiovisual presentation that includes one or more stimulus features. A feature extraction subsystem 325 identifies a plurality of features, such as features $f_1$ 326, $f_2$ 327, and $f_n$ 328, and captures each as a function of time. Data representing the extracted features are combined by an aggregator 345. As further described below, a filter 435 applies weights, such as weights $w_1$ 336, $w_2$ 337, and $w_n$ 338, are assigned to the extracted feature data to optimize the yield of the model. The resulting output is weighted, extracted feature data tracked over time, $y_1(t)$ 357.

In a particular aspect, the features are used as independent variables to which resulting physiological responses are correlated as dependent variables. In a visual presentation or a visual component of an audiovisual presentation, features extracted may include, for example, orientation energy, optical flow, luminance and chrominance, local spatial contrast, and temporal contrast. For an audio presentation or an audio component of an audio visual presentation, the features extracted may include pitch trajectory, sound envelope, speech envelope and spectral power or powers. The physiological responses may include data yielded by electroencephalography (EEG), electrocardiography (EKG), galvanic skin response, heart rate monitoring, respiration rate monitoring, eye tracking, and pupillometry.

Correspondingly, the subject 310 is presented with the stimulus 320 while being monitored by physiological measuring devices. In FIG. 3, the subject 310 is being monitored by an electroencephalography system that monitors physiological responses of the subject over time, including spatially-arrayed input leads features $x_1(t)$ 311, $x_2(t)$ 312, and $x_n(t)$ 313. A filter 315 applies weights, such as weights $v_1$ 316, $v_2$ 317, and $v_n$ 318 to the measured responses. Again, as further described below, the weights are assigned to the extracted feature data to optimize the yield of the model. Data representing the physiological responses are combined by an aggregator 325. The resulting output is weighted, physiological response data tracked over time, $y_2(t)$ 359.

The weighted, extracted feature data tracked over time, $y_1(t)$ 357, and the weighted, physiological response data tracked over time, $y_2(t)$ 359, is submitted to a correlator 355 and then an optimizer 365. Output of the optimizer 365 is fed back to the filters 315 and 335 to adjust the applied weights to improve the signal-to-noise ratio inherent in the correlated data, as well as to account for delays resulting from a subject's physiological response to various stimuli. In a particular aspect, a block-Toeplitz structure is used so that a temporal filter represented by the weights applied by the filter 335 filters across a temporal aperture, allowing for short-time integration of the multiple stimuli. In a particular aspect, a spatiotemporal matrix of EEG responses is constructed such that the filter 315 linearly filters one or more underlying neuronal sources. Temporally filtering the stimuli while spatially filtering the neuronal responses leads to pairs of optimal filters which uncover the covariation of specific temporal frequencies of the stimulus to specific neuronal sources or patterns of sources in the brain. For example, activity in an occipital component of the EEG may be found to covary with a visual stimulus feature, while activity in a temporal component may be found to covary with an audio stimulus feature. Each of these pairs is associated with an optimal correlation value, such as a generalized eigenvalue that conveys a level of physiological drive elicited by a selected identified stimulus.

The system may employ a variety of physiological responses recorded before, during and after a given stimulus. This includes, but is not limited to, recordings from EEG, EKG, Eye Tracking, Pupillometry, Heart Rate/Heart Rate Variability, GSR, and Respiratory Rate. A variety of models can be used to relate the physiological responses to the stimuli, including, but not limited to, temporal filters, spatial filters, spectral models, neural networks, and deep (learning) networks. These models all serve to learn an optimal representation between a set of computed stimuli and a corresponding set of physiological signals.

Figure 4:
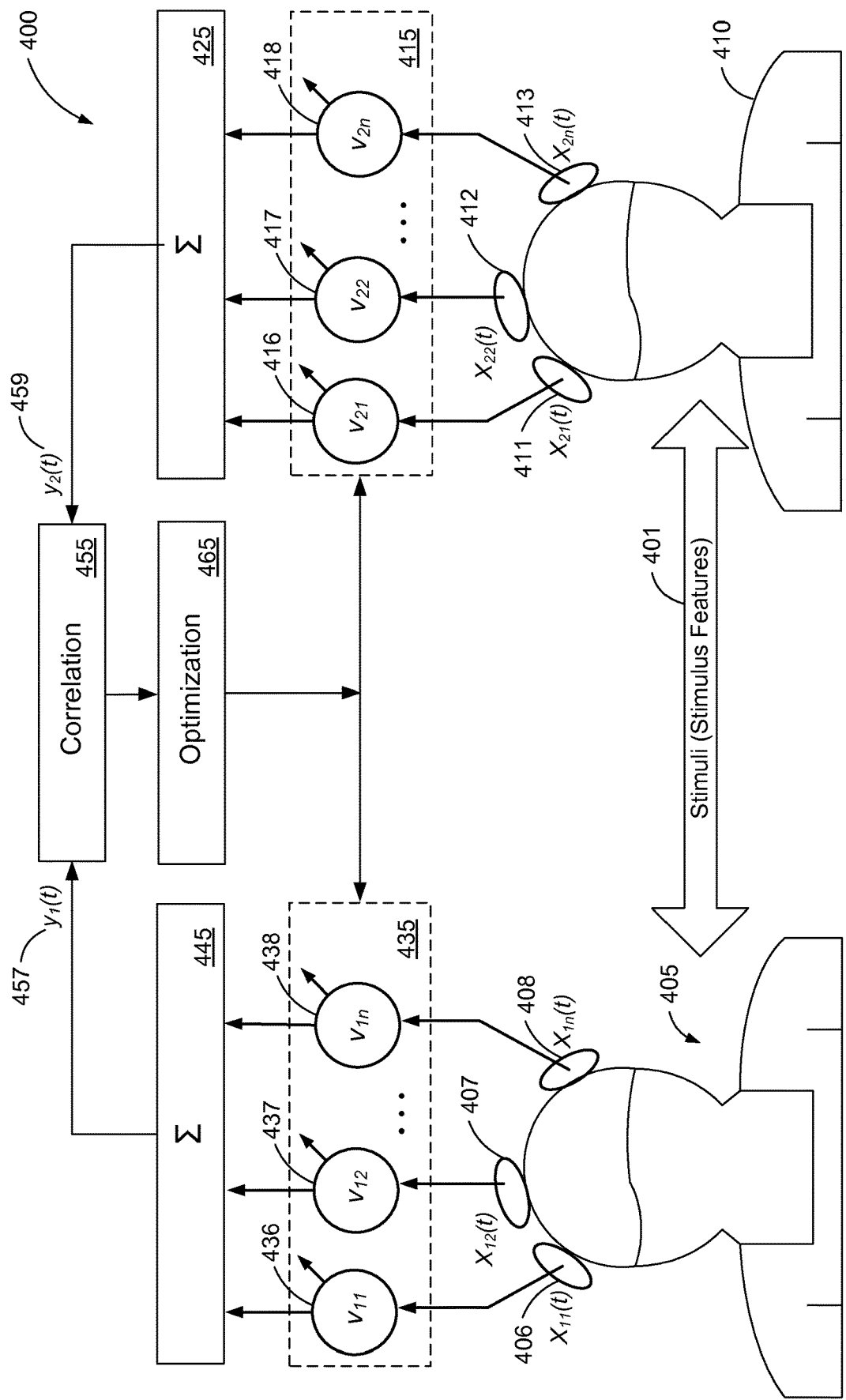

FIG. 4 is a block diagram of a system 400 that may be used to derive inter-subject correlation among a plurality of subjects. The system 400 shares many common elements with the system 300 of FIG. 3. However, the system 400 focuses on correlating physiological responses between subjects 405 and 410 in response to a stimulus including one or more stimulus features 401, rather than correlating physiological responses of a subject to one or more stimuli, as is the case in FIG. 3. It should be appreciated that the systems 300 and 400 may be combined to inter-relate responses of multiple subjects to a plurality of stimuli.

Each of the one or more subjects 405 and 410 are subjected to the stimulus 401. The subjects 405 and 410 are monitored by electroencephalography systems that monitor physiological responses of the subject over time. The subject 405 is monitored by spatially-arrayed input leads features $x_{11}(t)$ 406, $x_{12}(t)$ 407, and $x_{1n}(t)$ 408. A filter 435 applies weights, such as weights $v_{11}$ 436, $v_{12}$ 437, and $y_{1n}$ 438 to the measured responses. Data representing the physiological responses are combined by an aggregator 445. The resulting output is weighted, physiological response data tracked over time, $y_1(t)$ 457. The subject 410 is monitored by spatially-arrayed input leads features $x_{21}(t)$ 411, $x_{22}(t)$ 412, and $x_{2n}(t)$ 413. A filter 415 applies weights, such as weights $v_{21}$ 416, $v_{22}$ 417, and $v_{2n}$ 418 to the measured responses. Data representing the physiological responses are combined by an aggregator 425. The resulting output is weighted, physiological response data tracked over time, $y_2(t)$ 459.

The weighted physiological response feature data tracked over time, $y_1(t)$ 457 and the weighted, physiological response data tracked over time, $y_2(t)$ 459 are submitted to a correlator 455 and then an optimizer 465. Output of the optimizer 465 is fed back to the filters 415 and 435 to adjust the applied weights to improve the signal-to-noise ratio inherent in the correlated data, as well as to account for delays resulting from a subject's physiological response to various stimuli. The inter-subject data is correlated with the stimulus feature data (not shown in FIG. 4) to yield physiological response data collected from multiple subjects to the stimulus feature data.

Figure 5:
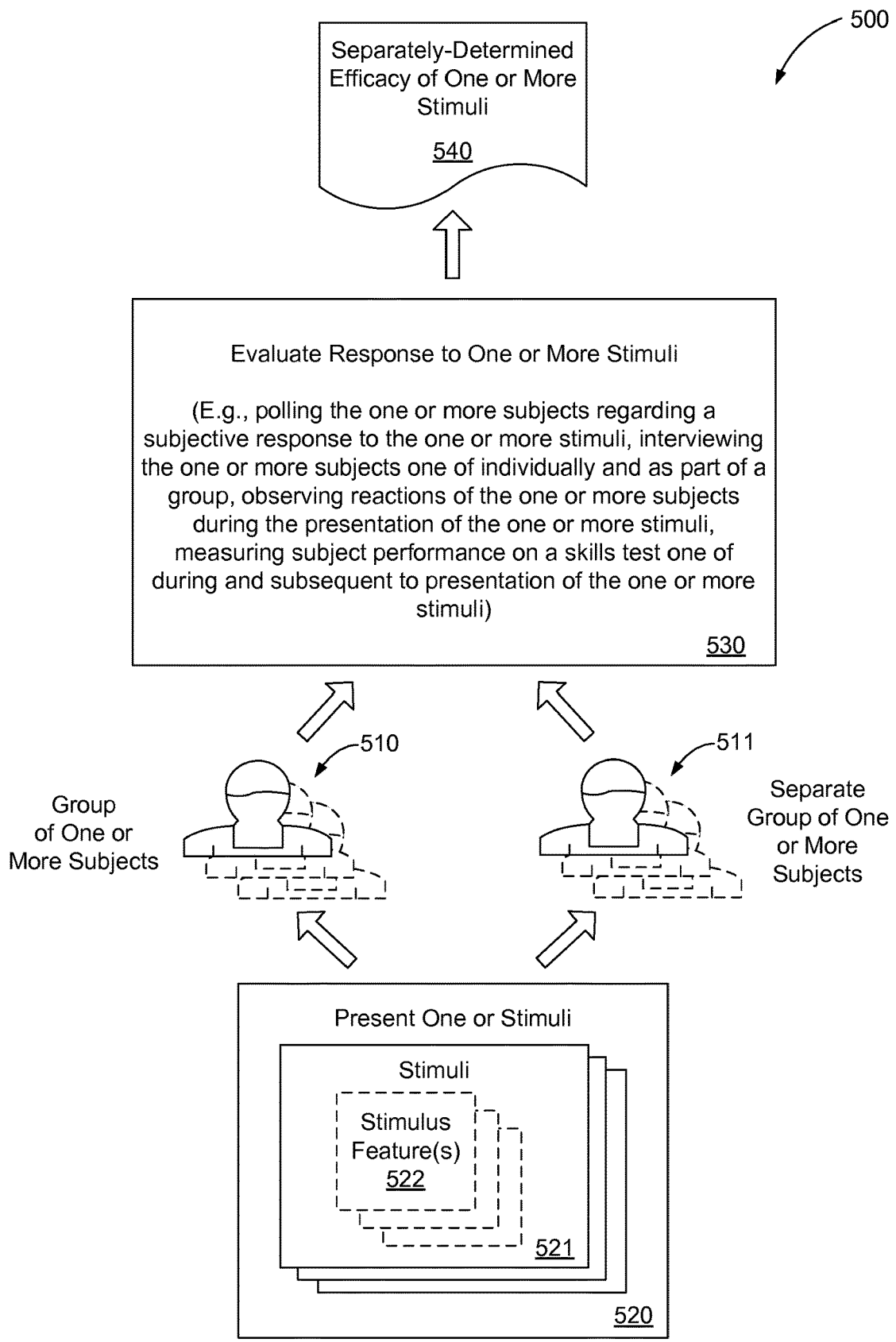
FIG. 5 is a schematic diagram of a process of assessing separately-determined efficacy of one or more stimuli according to aspects of the disclosure.

FIG. 5 is a schematic diagram of a process 500 of assessing separately-determined efficacy of one or more stimuli. To provide a body of information for association with the correlation between the physiological data and the stimuli, a group of one or more subjects 510, which may be the same group from which physiological data is acquired as described with reference to FIGS. 1 and 2, and/or a second group of one or more subjects 511, are subjected to a process 520 in which one or more stimuli 522 are presented. The stimuli, as previously described, may include one or more visual stimuli, audible stimuli, or a combination of visual and audible stimuli. Upon being subjected to the one or more stimuli subjects in the first group and/or the second group (if more than one group is used) are subjected to a process 530 to evaluate their response to the one or more stimuli. For example, the subjects may be polled regarding their subjective responses to the one or more stimuli. Also, the one or more subjects may be interviewed individually or as part of a group (e.g., a focus group) regarding their responses to the one or more stimuli. Further, the subjects may be observed to acquire their reactions to the one or more stimuli as the stimuli are presented. Alternatively, the one or more subjects may be submitted to testing to gauge their performance subsequent to or during the presentation of the stimuli to determine whether the stimuli have an effect on the subjects' cognitive performance on such testing. Additional methods of evaluating the response of subjects to the one or more stimuli also may be used. It should be appreciated that one or more of these methods of evaluating the subjects' responses may be used.

Figure 6:
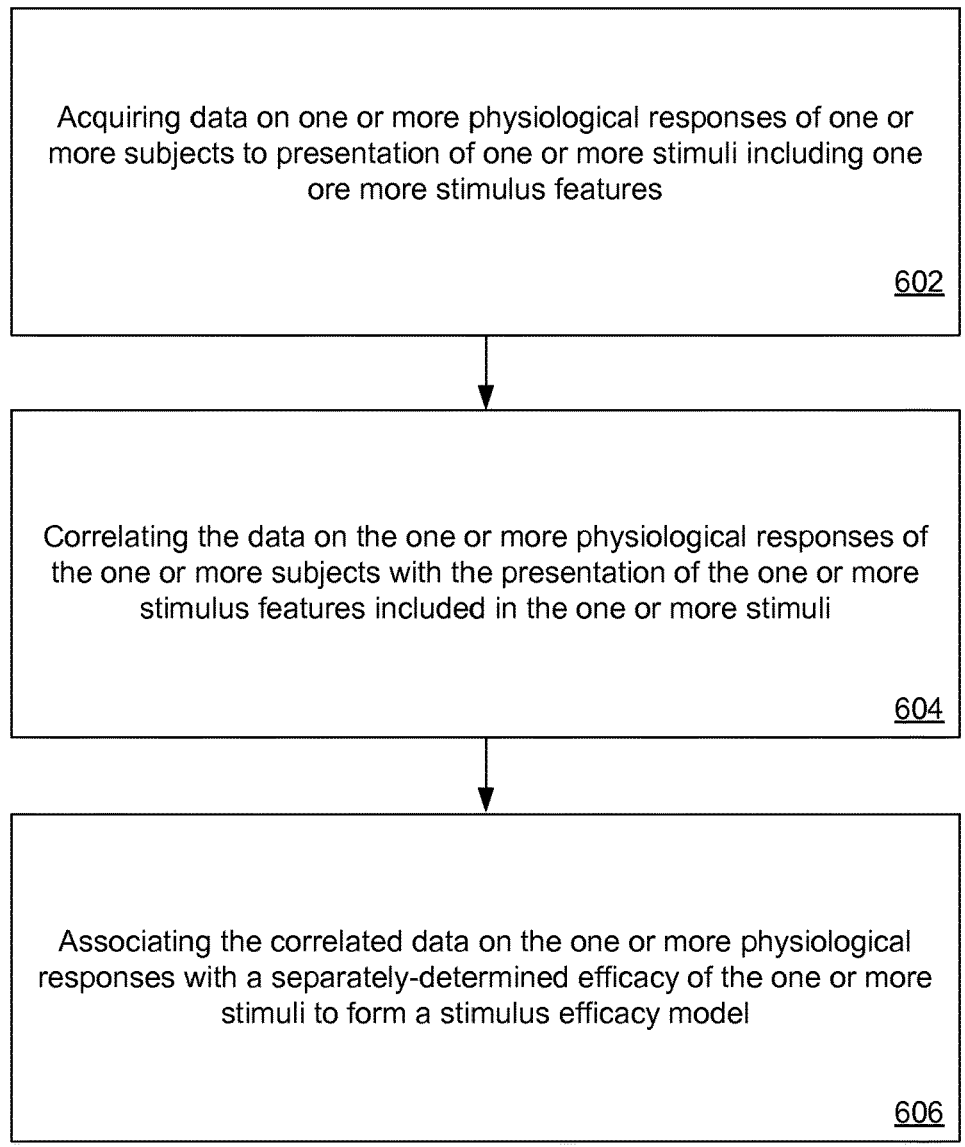
FIGS. 6-8 are flow diagrams of exemplary methods of acquiring and/or using data on physiological responses of one or more subjects to one or more stimuli including one or more stimulus features according to aspects of the disclosure.

FIG. 6 is a flow diagram of an exemplary method 600 of analyzing responses of one or more subjects to sets of stimuli according to aspects of the disclosure. At 602, data is acquired on one or more physiological responses of one or more subjects to presentation of one or more stimuli including one or more stimulus features. As previously described with reference to FIGS. 1-4, the data may be acquired by EKG, GSR, heart rate, respiration rate, eye-gaze, fixation duration, pupilometry, or other measurements. At 604, the data on the one or more physiological responses of the one or more subjects are correlated with the presentation of the one or more stimulus features included in the one or more stimuli. At 606, the correlated data on the one or more physiological responses are associated with a separately-determined efficacy of the one or more stimuli to form a stimulus efficacy model. As a result, a projected efficacy of a stimulus is determinable from one or more subsequently-measured physiological responses to the stimulus.

Figure 7:
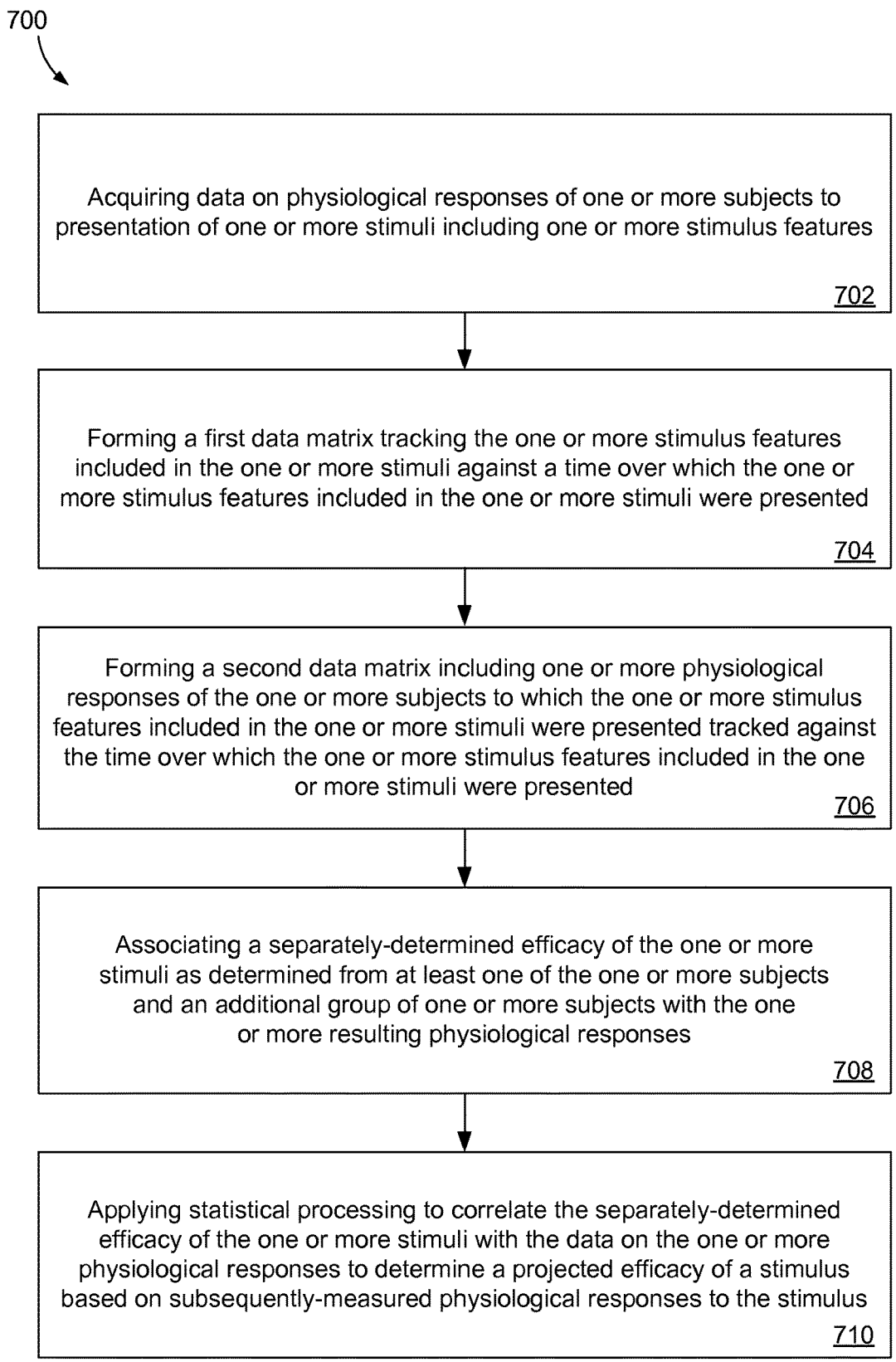

FIG. 7 is a flow diagram of an exemplary method 700 of analyzing responses of one or more subjects to sets of stimuli according to aspects of the disclosure. At 702, data is acquired on physiological responses of one or more subjects to presentation of one or more stimuli including one or more stimulus features. As previously described with reference to FIGS. 1-4, the data may be acquired by EKG, GSR, heart rate, respiration rate, eye-gaze, fixation duration, pupilometry, or other measurements. At 704, a first data matrix is formed, where the first matrix includes one or more stimulus features included in the one or more stimuli tracked against a time over which the one or more stimuli were presented. At 706, a second data matrix is formed that includes one or more physiological responses of a first group of one or more subjects that were exposed to the one or more stimulus features included in the one or more stimuli tracked against the time over which the one or more stimuli were presented. At 708, a separately-determined efficacy of the set of stimuli as determined from at least one of the first group of one or more subjects and a second group of one or more subjects are associated with the one or more resulting physiological responses. The separately-determined efficacy is measured by polling, interviewing, observing, testing, or other methods as described with reference to FIG. 6. At 710, statistical processing is applied to correlate the separately-determined efficacy of the set of stimuli with the one or more physiological responses to determine a projected efficacy of a stimulus based on subsequently-measured physiological responses.

Figure 8:
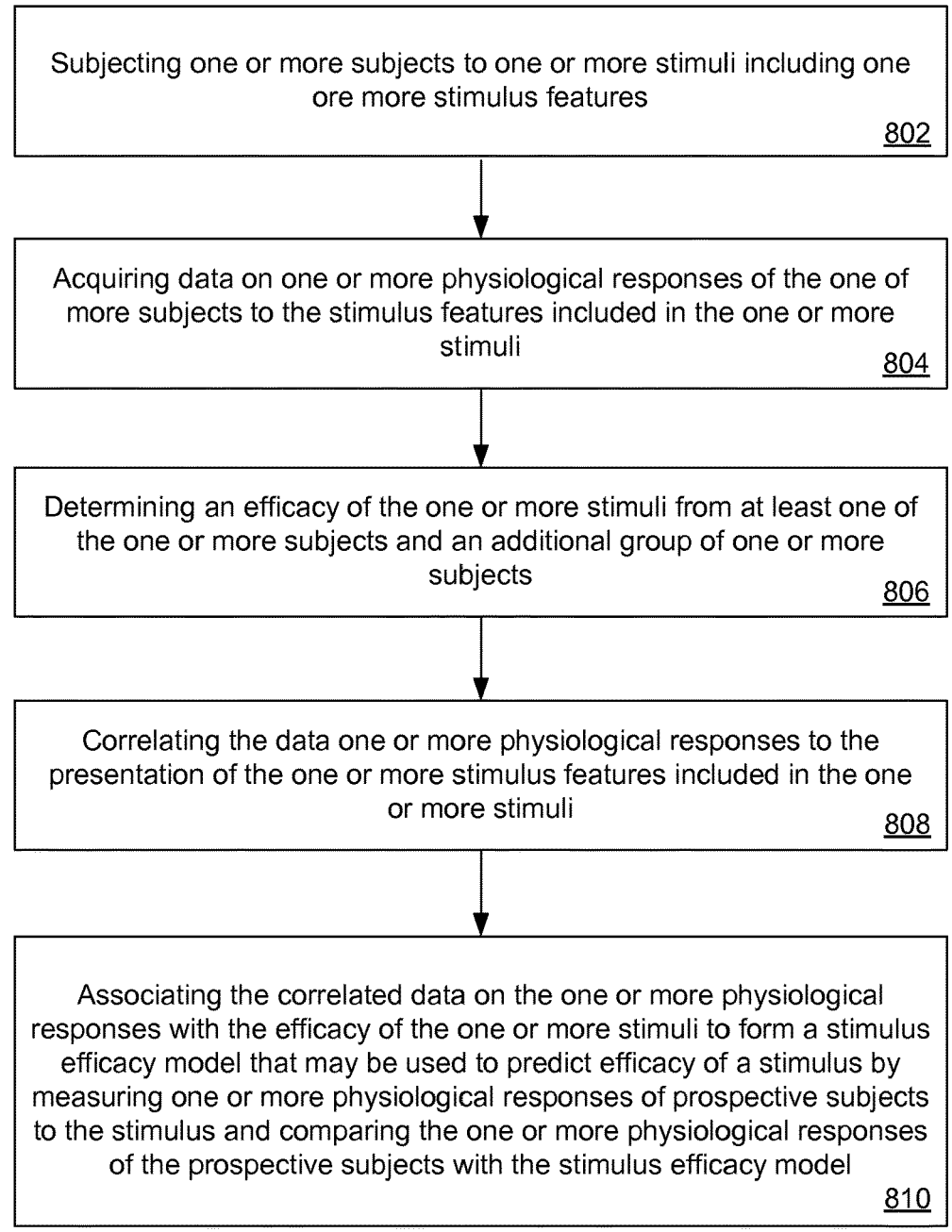

FIG. 8 is a flow diagram of another exemplary method of analyzing responses of one or more subjects to sets of stimuli according to aspects of the disclosure. At 802, one or more subjects are subjected to one or more stimuli including one or more stimulus features. At 804, data on one or more physiological responses of the one of more subjects to the one or more stimulus features included in the one or more stimuli are acquired. As previously described with reference to FIGS. 1-4, the data may be acquired by EKG, GSR, heart rate, respiration rate, eye-gaze, fixation duration, pupilometry, or other measurements. At 806, efficacy of one or more stimuli from at least one of the one or more subjects and an additional group of one or more subjects is determined. The separately-determined efficacy is measured by polling, interviewing, observing, testing, or other methods as described with reference to FIG. 5. At 808, a model correlating the one or more measurable physiological responses to the presentation of the one or more stimulus features included in the one or more stimuli is generated. At 810, the model is correlated with the efficacy of the one or more stimuli. The model may be used to determine prospective efficacy of a stimulus by subjecting one or more additional subjects to the stimulus and measuring the one or more measurable physiological responses of the one or more additional subjects.

Figure 9:
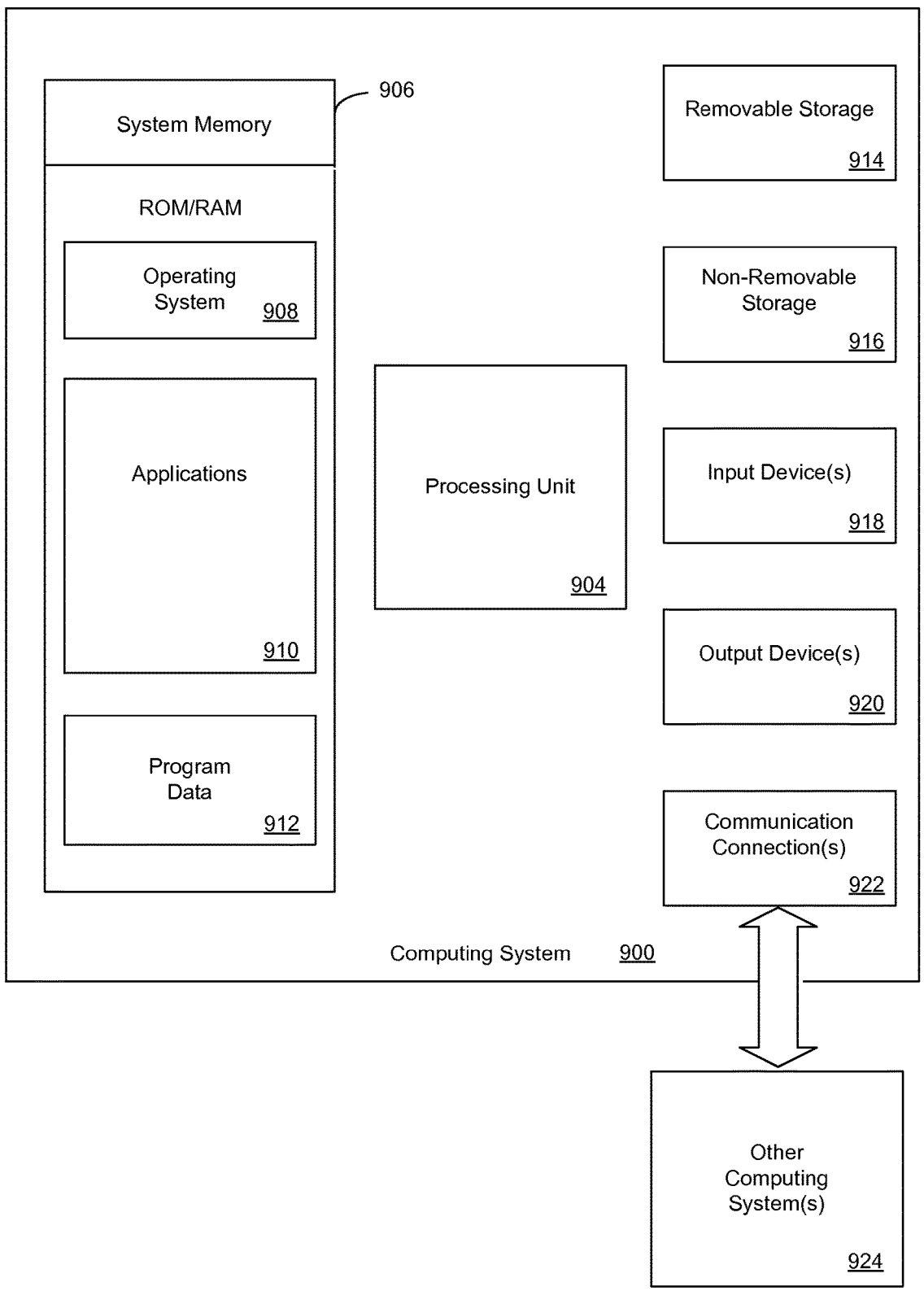
FIG. 9 is a block diagram of an exemplary computing system that may be used to acquire and process data on physiological responses to one or more stimuli including one or more stimulus features and data on separately-determined efficacy of the one or more stimuli according to aspects of the disclosure.

FIG. 9 is a block diagram of an exemplary computing system 900 that may be used for performing computer-implemented methods or executing computer-executable instructions for generating or using a model correlating physiological responses with one or more stimuli including one or more stimulus features according to the present disclosure.

Referring to FIG. 9, the computing system 900 may include any of a number of forms of stationary or mobile computing devices. The computing device 900 typically includes at least one processing unit 904 and a system memory 906. Depending on the exact configuration and type of computing device, the system memory 906 may be volatile (such as RAM), non-volatile (such as ROM, flash memory, and the like) or some combination of the two. The system memory 906 typically maintains an operating system 908, one or more applications 910, and program data 912.

The computing device 900 may also have additional features or functionality. For example, the computing device 900 may also include additional data storage devices (removable and/or non-removable) such as, for example, magnetic disks, optical disks, or tape. Such additional storage is illustrated in FIG. 9 by removable storage 914 and non-removable storage 916. Computer storage media may include volatile and non-volatile, removable and non-removable media implemented in any method or technology for storage of information, such as computer readable instructions, data structures, program modules or other data. The system memory 906, the removable storage 914, and the non-removable storage 916 are all examples of computer storage media. Available types of computer storage media include, but are not limited to, RAM, ROM, EEPROM, flash memory (in both removable and non-removable forms) or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing device 900. Any such computer storage media may be part of the computing device 1000.

The computing device 1000 may also have input device(s) 918 such as a keyboard, mouse, pen, voice input device, touch input device, etc. Further, in accordance with aspects of the present disclosure, physiological measurement devices to track EEG, EKG, heart rate, respiration rate, eye-gaze, fixation duration, pupilometry, or other measurements may be operatively coupled as input devices to the computing device 900 to acquire physiological data. Output device(s) 920 such as a display, speakers, printer, etc., may also be included. In accordance with aspects of the disclosure, such devices may be used to present the one or more stimuli. The computing device 900 thus may be used to present stimuli, capture physiological data, and correlate the data with the stimuli and included stimulus features. The computing device 900 may also be used to receive separately-determined data on the efficacy of the stimulus. Similarly, suitable computer-readable instructions may be used to generate models and perform statistical processing on the data in accordance with aspects of the disclosure.

The computing device 900 also may include one or more communication connections 922 that allow the computing device 900 to communicate with other computing devices 924, such as over a network or a wireless network. The one or more communication connections 922 are an example of communication media. Available forms of communication media typically carry computer readable instructions, data structures, program modules or other data in a modulated data signal such as a carrier wave or other transport mechanism and includes any information delivery media. The term "modulated data signal" may include a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The term computer readable media as used herein includes both storage media and communication media.

While the disclosure has been has been set forth herein in reference to specific aspects, features and illustrative aspects, it will be appreciated that the utility of the disclosure is not thus limited, but rather extends to and encompasses numerous other variations, modifications and alternative aspects, as will suggest themselves to those of ordinary skill in the field of the present disclosure, based on the description herein. Any of various elements or features recited herein is contemplated for use with other features or elements disclosed herein, unless specified to the contrary. Correspondingly, the invention that may be hereinafter claimed is intended to be broadly construed and interpreted, as including all such variations, modifications and alternative aspects, within its spirit and scope.

What is claimed is:

1. A computer-implemented method to determine an efficacy of a stimulus, the method comprising:
    providing a computing system comprising an output device and an input device operatively coupled to one or more sensors;
    subjecting one or more subjects to one or more stimuli displayed on the output device;
    acquiring at least a first set of data and a second set of data by:
        measuring, via the one or more sensors, one or more physiological responses to the one or more stimuli including one or more stimulus features;
        recording via the one or more sensors the one or more physiological responses measured,
        wherein the first set of data is associated with the one or more stimulus features of at least one of the one or more stimuli presented to the one or more subjects and the second set of data is associated with the one or more physiological responses of the one or more subjects to presentation of the one or more stimuli including the one or more stimulus features;
        wherein the first set of data includes weighted, extracted stimulus feature data comprising data associated with the one or more stimulus features during presentation of the respective stimuli and captured as a function of time and further weighted via a first filter comprising a temporal element;
        wherein the second set of data includes weighted, physiological response data comprising data associated with the one or more physiological responses measured and recorded via the one or more sensors and weighted via a second filter comprising a spatial element;
    correlating the first and second sets of data, the data in the first set having been weighted by the first filter comprising the temporal element and the data in the second set having been weighted by the second filter comprising the spatial element;
    associating the correlated data with a separately-determined efficacy of the one or more stimuli to form a stimulus efficacy model; and
    determining a projected efficacy of a second stimulus by comparing one or more subsequently-measured physiological response to the stimulus with the stimulus efficacy model.

2. The method of claim 1, wherein the measuring of the one or more physiological responses to the one or more stimuli including the one or more stimulus features includes one or more of:
    electroencephalography (EEG);
    electrocardiography (EKG);
    galvanic skin response;
    heart rate monitoring;
    respiration rate monitoring;
    eye tracking; and
    pupillometry.

3. The method of claim 1, wherein the correlating of the data on the one or more physiological responses of the one or more subjects with the presentation of the one or more stimulus features included in the one or more stimuli includes forming a first data matrix tracking the presentation of each of the one or more stimuli including the one or more stimulus features over a period of time during which the one or more stimuli are presented.

4. The method of claim 3, wherein the correlating of the data on the one or more physiological responses of the one or more subjects with the presentation of the one or more stimulus features included in the one or more stimuli includes forming a second data matrix representing a quantified measure of each of the one or more physiological responses over the time period over which the one or more stimuli are presented.

5. The method of claim 1, wherein the one or more stimuli include at least one of one or more audio stimuli and one or more visual stimuli.

6. The method of claim 5, wherein the one or more stimuli include one or more audio stimuli, and the one or more stimulus features include at least one of:
    pitch trajectory;
    sound envelope;
    speech envelope;
    spectral power;
    rhythm;
    volume; and
    pitch.

7. The method of claim 5, wherein the one or more stimuli include one or more visual stimuli, and the one or more stimulus features include at least one of:
    orientation energy;
    optical flow;
    luminance;
    chrominance;

local spatial contrast; and temporal contrast.

8. The method of claim 1, further comprising quantifying a magnitude of the one or more stimulus features included in the one or more stimuli.

9. The method of claim 8, wherein the quantified magnitude of the one or more stimulus features is collected by a feature extractor.

10. The method of claim 1, wherein the separately-determined efficacy of the one or more stimuli is determined from at least one of the one or more subjects and an additional group of one or more subjects regarding one or more subjective responses to the one or more stimuli.

11. The method of claim 1, wherein the separately-determined efficacy of the one or more stimuli ascertained is determined by one or more of:

polling the one or more subjects regarding a subjective response to the one or more stimuli;

interviewing the one or more subjects individually and as part of a group regarding the one or more stimuli;

observing reactions of the one or more subjects during the presentation of the one or more stimuli; and measuring subject performance on a skills test during and subsequent to presentation of the one or more stimuli.

* * * * *